(12) United States Patent
Vogt et al.

(10) Patent No.: US 8,246,598 B2
(45) Date of Patent: Aug. 21, 2012

(54) ABSORBENT ARTICLE

(75) Inventors: Robert E. Vogt, Neenah, WI (US);
Keith R. Haen, Neenah, WI (US);
James A. Boldra, Menasha, WI (US);
Allen J. Dohnalik, DePere, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1769 days.

(21) Appl. No.: 11/262,008

(22) Filed: Oct. 28, 2005

(65) Prior Publication Data
US 2007/0100312 A1 May 3, 2007

(51) Int. Cl.
*A61F 13/15* (2006.01)
(52) U.S. Cl. .......................................... 604/391; 604/387
(58) Field of Classification Search .............. 604/385.01, 604/386–387, 391–392
See application file for complete search history.

(56) References Cited

U.S. PATENT DOCUMENTS

| | | | |
|---|---|---|---|
| 3,769,978 A * | 11/1973 | DeNight et al. ............... 604/374 |
| 4,663,220 A | 5/1987 | Wisneski et al. |
| 4,704,116 A | 11/1987 | Enloe |
| 4,798,603 A | 1/1989 | Meyer et al. |
| 5,114,781 A | 5/1992 | Morman |
| 5,116,662 A | 5/1992 | Morman |
| 5,176,668 A | 1/1993 | Bernardin |
| 5,192,606 A | 3/1993 | Proxmire et al. |
| 5,226,992 A | 7/1993 | Morman |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,577,540 A | 11/1996 | Sageser |
| 5,645,542 A | 7/1997 | Anjur et al. |
| 5,883,028 A | 3/1999 | Morman et al. |
| 5,964,743 A | 10/1999 | Abuto et al. |
| 6,231,557 B1 | 5/2001 | Krautkramer et al. |
| 6,318,555 B1 | 11/2001 | Kuske et al. |
| 6,362,389 B1 | 3/2002 | McDowall et al. |
| 6,514,233 B1 | 2/2003 | Glaug |
| 6,552,245 B1 | 4/2003 | Roessler et al. |
| 2002/0138056 A1 | 9/2002 | Kuen et al. |
| 2003/0111168 A1 | 6/2003 | Olson et al. |
| 2004/0122413 A1 | 6/2004 | Roessler et al. |
| 2005/0256495 A1 | 11/2005 | Schlinz et al. |
| 2006/0246248 A1 | 11/2006 | Van Dyke |

FOREIGN PATENT DOCUMENTS

| | | |
|---|---|---|
| EP | 0 217 032 A2 | 4/1987 |
| WO | WO 97/47265 A1 | 12/1997 |
| WO | WO 00/35776 A1 | 6/2000 |
| WO | WO 01/88245 A2 | 11/2001 |
| WO | WO 03/051254 A2 | 6/2003 |

\* cited by examiner

*Primary Examiner* — Michele M Kidwell
(74) *Attorney, Agent, or Firm* — John L. Brodersen; Randall W. Fieldhack

(57) ABSTRACT

An absorbent article including an absorbent chassis and a pair of back ears. The absorbent chassis includes a liquid impermeable outercover and an absorbent body disposed on said outercover. A least a portion of each back ear is substantially flush with the chassis back waist edge.

10 Claims, 5 Drawing Sheets

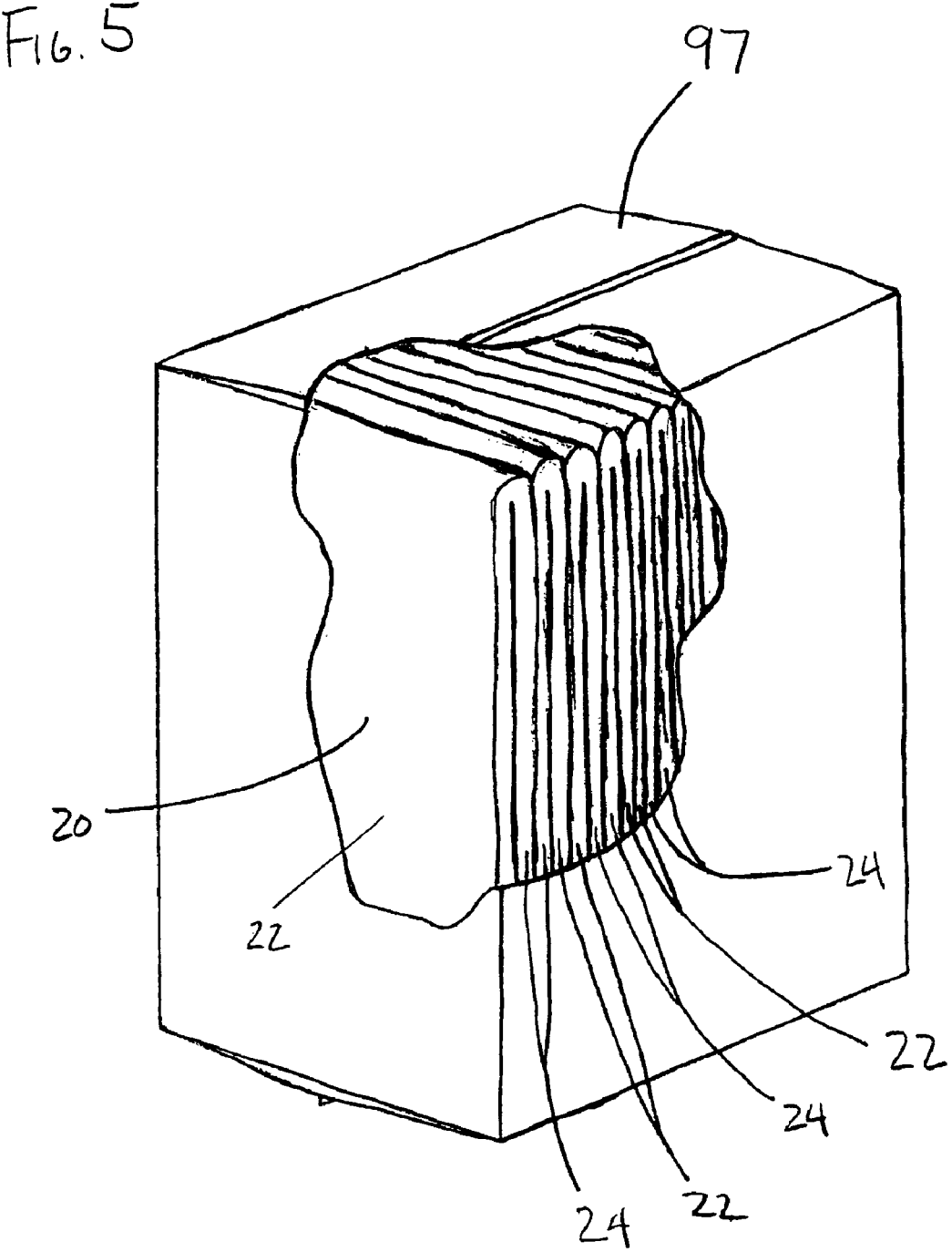

ABSORBENT ARTICLE

BACKGROUND OF THE INVENTION

The present invention relates to disposable absorbent articles. More specifically, the invention relates to a disposable absorbent article, such as a disposable diaper, that includes a pair of back ears and that is designed to be produced at a high speed and yet in a reliable and economical fashion.

Absorbent articles such as disposable diapers are typically made on high speed (i.e., hundreds of products per minute) production lines. When manufacturing articles in this way, it is desirable to produce a product that includes features that provide an attractive product to the caregiver and/or the user and that is effective at containing and absorbing bodily exudates. An example of such features include separately attached ears. In certain aspects, the articles can include a pair of ears extending from the article in the back waist region. In addition, these articles can optionally include a pair of ears extending from the article in the front waist region. The ears can be useful for providing better hip coverage to the wearer. Further, the ears can optionally be stretchable or even elastomeric for improved fit and comfort. Moreover, the ears can include fastening members to keep the article about the hips and waist of the wearer.

While absorbent articles that include features such as separately attached ears or other components can be desirable in certain circumstances, adding components to a mass produced absorbent article can be costly and increase the complexity of the production process thereby potentially creating a speed limitation to the process. Moreover, there is an increasing desire to produce effective absorbent articles very inexpensively keeping in mind the more cost-conscious consumer.

Thus, there is a need for an absorbent article that is configured to be made on a high-speed production line that includes back ears and optionally front ears. Further, there is a need for such an article that is configured to be produced in a very efficient and cost-effective manner. Still further, there is a need for such an article that can be inexpensively made and yet is still pleasing to the wearer and/or caregiver.

SUMMARY OF THE INVENTION

In one aspect, the present invention is directed to an absorbent article defining a lateral direction and a longitudinal direction perpendicular to the lateral direction, a back waist region, a front waist region and a crotch region connecting the back waist region and the front waist region, and an inner surface and an outer surface opposite the inner surface. The absorbent article includes an absorbent chassis defining a chassis back waist edge and a chassis front waist edge opposite the chassis back waist edge, a pair of chassis side edges extending in the longitudinal direction, and a substantially rectangular chassis shape. The absorbent chassis includes a liquid impermeable outercover and an absorbent body disposed on the outercover. The absorbent article also includes a back ear formed separately from and attached proximate each of the chassis side edges in the back waist region. Each of the back ears includes a back ear proximal edge, a back ear distal edge, a back ear first connecting edge and a back ear second connecting edge, where the back ear first connecting edge and the back ear second connecting edge connect the back ear proximal edge and the back ear distal edge. Further, the back ear first connecting edges of each of the back ears are substantially flush with the chassis back waist edge. The absorbent article also includes a fastening member disposed on the inner surface of each of the pair of back ears.

In another aspect, the present invention is directed to an absorbent article defining a lateral direction and a longitudinal direction perpendicular to the lateral direction, a back waist region, a front waist region and a crotch region connecting the back waist region and the front waist region, and an inner surface and an outer surface opposite the inner surface. The absorbent article includes an absorbent chassis defining a chassis back waist edge and a chassis front waist edge opposite the chassis back waist edge, a pair of chassis side edges extending in the longitudinal direction where the chassis side edges are rectilinear edges. The absorbent chassis including a liquid impermeable outercover and an absorbent body disposed on the outercover. The absorbent article also includes a back ear formed separately from and attached proximate each of the chassis side edges in the back waist region. Each of the back ears includes a back ear proximal edge, a back ear distal edge, a back ear first connecting edge and a back ear second connecting edge, where the back ear first connecting edge and the back ear second connecting edge connect the back ear proximal edge and the back ear distal edge. In addition, the back ear first connecting edges of each of the back ears are substantially flush with the chassis back waist edge. The absorbent article also includes a fastening member disposed on each of the pair of back ears. Each of the fastening members defines a fastener first connecting edge, a fastener second connecting edge, a fastener proximal edge and a fastener distal edge. The fastener first connecting edge and the fastener second connecting edge connect the fastener proximal edge and the fastener distal edge. In addition, each of the fastener first connecting edges are substantially flush with the back ear first connecting edge on which each of the fastening members are disposed.

In yet another aspect, the present invention is directed to a package of absorbent articles including a package and a plurality of absorbent articles disposed within the package. Each of the absorbent articles defines a lateral direction and a longitudinal direction perpendicular to the lateral direction, a back waist region, a front waist region and a crotch region connecting the back waist region and the front waist region. Each of the absorbent articles includes an absorbent chassis defining a back waist edge and a front waist edge opposite the back waist edge, a pair of chassis side edges extending in the longitudinal direction, and a substantially rectangular chassis shape. The absorbent chassis includes a liquid impermeable outercover and an absorbent body disposed on the outercover. Each of the absorbent articles also includes a back ear formed separately from and attached proximate each of the chassis side edges in the back waist region and a fastening member disposed on each of the pair of back ears. Each of the absorbent articles are configured in the package such that the front waist region of a first absorbent article is in a facing relationship with the front waist region of a first adjacent absorbent article. In addition, the back waist region of the first absorbent article is in a facing relationship with the back waist region of a second adjacent absorbent article to define a front-front, back-back article packaging pattern.

The above-mentioned and other aspects of the present invention will become more apparent, and the invention itself will be better understood by reference to the drawings and the following description of the drawings.

BRIEF DESCRIPTION OF THE DRAWINGS

FIG. 5 representatively illustrates a perspective view of a package of articles, with portions of the package cut away to show the articles therein.

Corresponding reference characters indicate corresponding parts throughout the drawings.

DEFINITIONS

Figure 1:
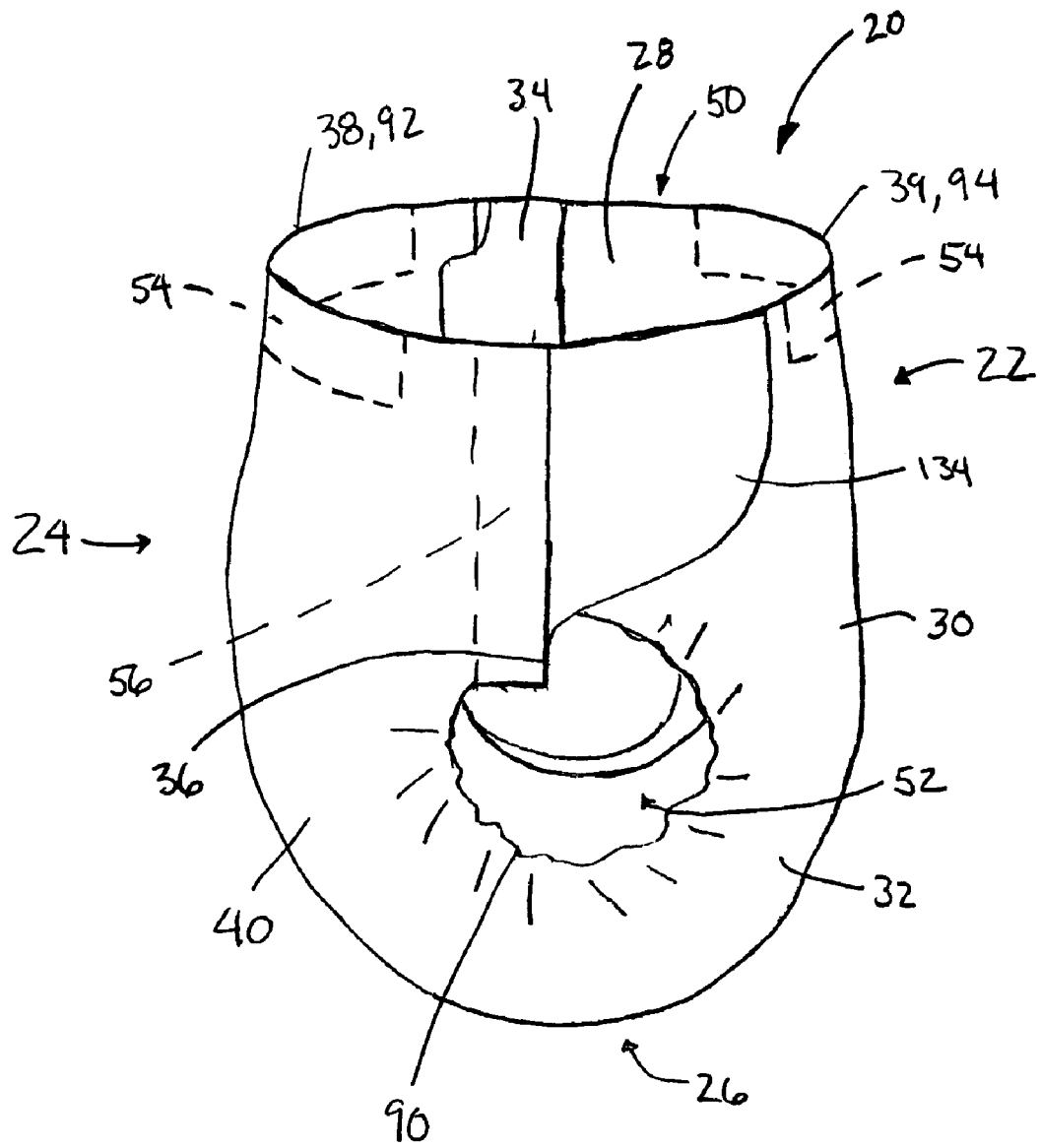
FIG. 1 representatively illustrates a side view of a diaper of the present invention with a fastening member of the diaper in a fastened configuration.

Within the context of this specification, each term or phrase below includes the following meaning or meanings:

"Attach" and its derivatives refer to the adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Connect" and its derivatives refer to the adhering, bonding, attaching, sewing together, or the like, of two elements. Two elements will be considered to be connected together when they are integral with one another or connected directly to one another or indirectly to one another, such as when each is directly connected to intermediate elements. "Connect" and its derivatives include permanent, releasable, or refastenable connection.

"Complementary shape" when used in the context to describe ears refers to the configuration of the ear allowing it to be nested with another ear with a minimum of gapping between the ears such that if the two ears were to be cut from a web of material there would not be any trim waste material resulting from spacing between the ears.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 50 percent (to 150 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Join" and its derivatives refer to the adhering, bonding, sewing together, or the like, of two separate elements. Two elements will be considered to be joined together when they are joined directly to one another or indirectly to one another, such as when each is directly joined to intermediate elements. "Join" and its derivatives include permanent, releasable, or refastenable joinder.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Stretchable" means that a material can be stretched, without breaking, by at least 50 percent (to 150 percent of its initial (unstretched) length) in at least one direction. Elastic materials and extensible materials are each stretchable materials.

"superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Referring now to the drawings and in particular to FIG. 1, an absorbent article of the present invention is representatively illustrated in the form of baby diaper and is indicated in its entirety by the reference numeral 20. The diaper 20 includes a pair of back ears 134, and can optionally include a pair of front ears 34. The diaper 20 may suitably be disposable, which refers to articles that are intended to be discarded after a limited period of use instead of being laundered or otherwise conditioned for reuse. It should also be understood that the present invention is suitable for use with various other absorbent articles intended for personal wear, including but not limited to children's training pants, feminine hygiene products, incontinence products, medical garments, surgical pads and bandages, other personal care or health care garments, and the like without departing from the scope of the present invention.

By way of illustration only, various materials and methods for constructing diapers such as the diapers 20 of the various aspects of the present invention are disclosed in U.S. patent application Ser. No. 10/836,490, filed Apr. 29, 2004, in the name of Schlinz et al.; U.S. Pat. No. 5,496,298 issued Mar. 5, 1996, to Kuepper et al.; U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et al., and U.S. Pat. No. 5,509,915 issued Apr. 23, 1996, to Hanson et al., each of which are incorporated herein by reference to the extent that they are consistent (i.e., not in conflict) herewith.

Figure 2:
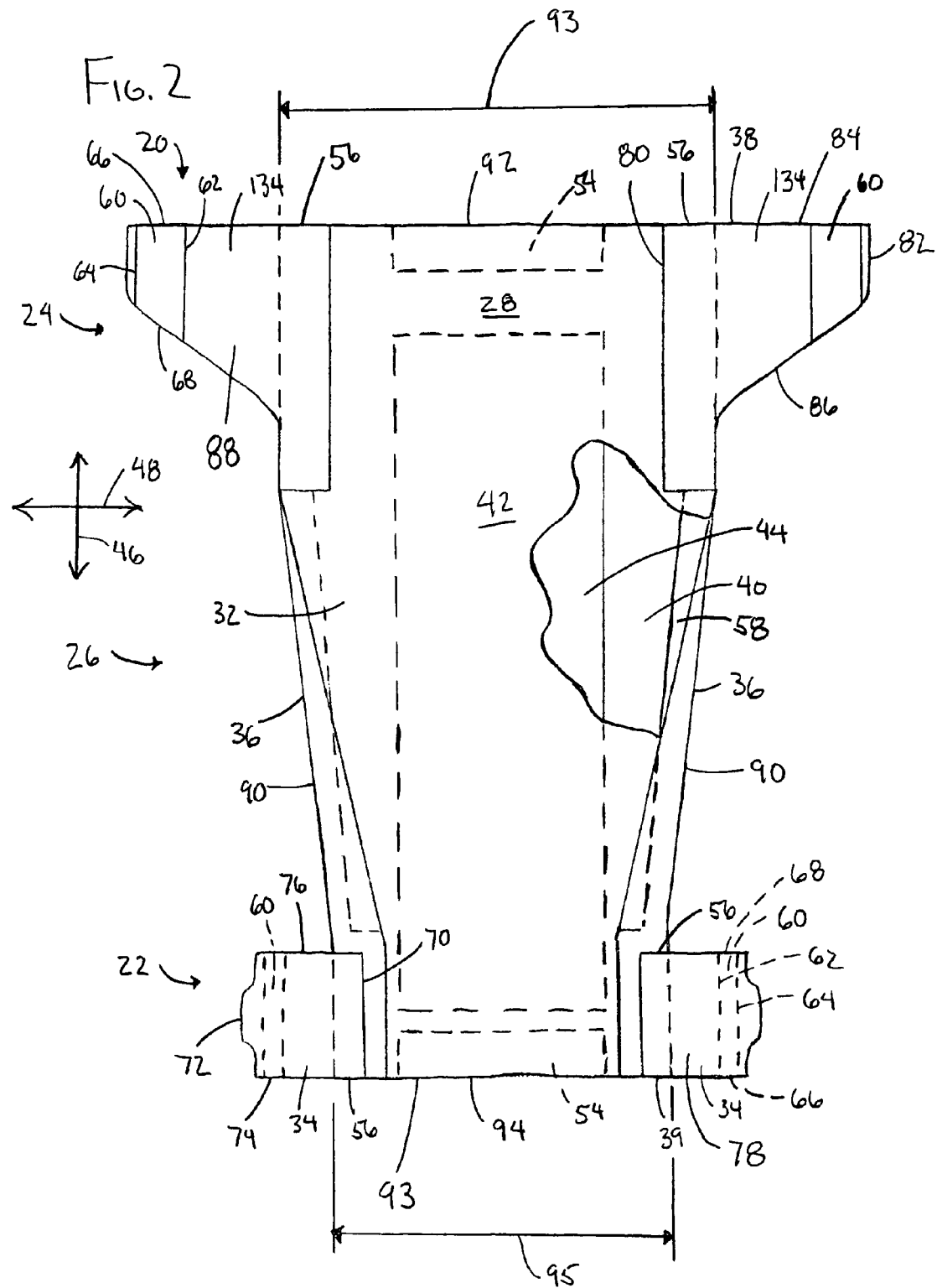
FIG. 2 representatively illustrates a plan view of a diaper similar to that of FIG. 1 in an unfastened, stretched and laid flat condition, and showing the surface of the diaper that faces the wearer with portions cut away to show underlying features.
Figure 3:
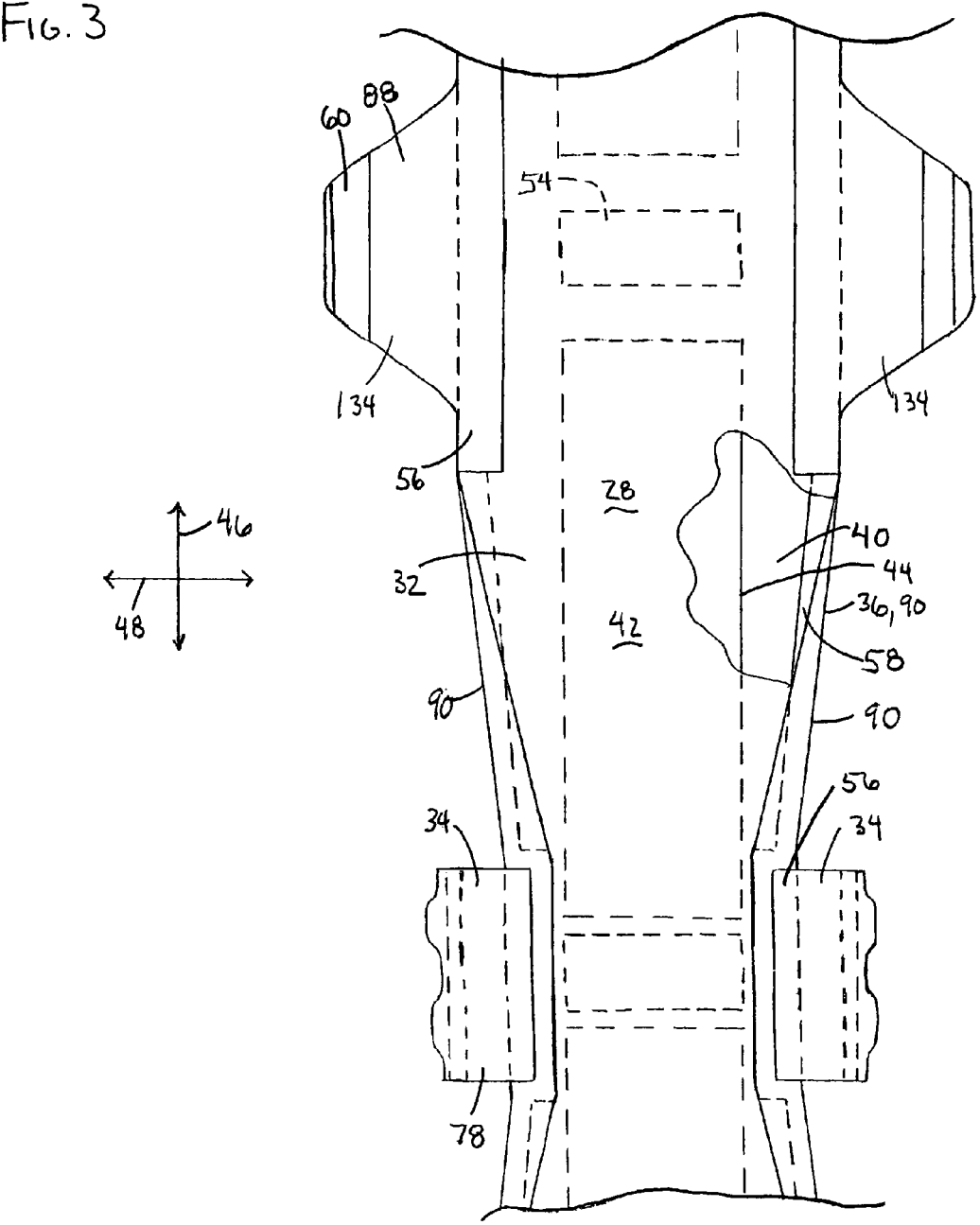
FIG. 3 representatively illustrates a plan view of an interconnected web of diapers of the present invention in a front-front, back-back configuration.

The diaper 20 is illustrated in FIG. 1 in a fastened condition. The diaper 20 defines a longitudinal direction 46 and a lateral direction 48 perpendicular to the longitudinal direction as shown in FIGS. 2 and 3. The diaper 20 further defines a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 includes those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The diaper 20 also define an inner surface 28 adapted in use to be disposed toward the wearer, and an outer surface 30 opposite the inner surface. With additional reference to FIGS. 2 and 3, the diaper 20 has a pair of laterally opposite article side edges 36 extending in the longitudinal direction 46 and a pair of longitudinally opposite waist edges referred to herein as the article back waist edge 38 and the article front waist edge 39.

The illustrated diaper 20 can include an absorbent chassis, generally indicated at 32. The absorbent chassis 32 can define a pair of laterally opposite chassis side edges 90 extending in the longitudinal direction 46 and a pair of longitudinally opposite chassis waist edges referred to herein as the chassis back waist edge 92 and the chassis front waist edge 94.

For example, in the aspect of FIGS. 1-3, the diaper 20 includes a substantially rectangular absorbent chassis 32 and ears 34, 134 formed separately from and attached to the absorbent chassis 32 along the chassis side edges 90. The ears 34, 134 can be attached along seams 56 proximate the chassis side edges 90 of the absorbent chassis 32 in the respective front and back waist regions 22 and 24 of the diaper 20. More particularly, the pair of back ears 134 can be permanently attached to and extend laterally from the absorbent chassis 32 at the back waist region 24, and in aspects where the diaper 20 includes front ears 34, the pair of front ears 34 can be permanently attached to and extend laterally outward from the absorbent chassis 32 at the front waist region 22. The ears 34 and 134 may be attached to the absorbent chassis 32 using means known to those skilled in the art such as adhesive, thermal bonding, pressure bonding, ultrasonic bonding, and the like or combinations thereof.

The absorbent chassis 32 is illustrated in FIGS. 1-3 as having a substantially rectangular shape. As used herein, the term "Substantially Rectangular" when used to describe the absorbent chassis 32 indicates that the chassis includes rectilinear chassis side edges 90 and chassis waist edges 92 and 94. As such, the respective edges 90, 92 and 94 are characterized by a straight line or multiple straight lines rather than including curvilinear portions and as such, can be more efficient to manufacture. Nonetheless, as can be readily appreciated, certain processing, such as folding or inflecting of the various chassis edges 90, 92 and 94 can occur and the chassis 32 may still be substantially rectangular. Such a configuration can advantageously reduce the complexity of the process for producing the diapers 20 and increase the speed of the process, as cutting or providing curvilinear shaping and/or removing portions of an absorbent chassis 32 can be speed limiters within a diaper production process.

The absorbent chassis 32 can include an outercover 40 and a bodyside liner 42 (FIGS. 2-3) in a superposed relation therewith. The liner 42 can be suitably joined to the outercover 40 along at least a portion of the absorbent chassis 32. The liner 42 can be suitably adapted, i.e., positioned relative to the other components of the diaper 20, to contact the wearer's skin during wear of the diaper. The absorbent chassis 32 also includes an absorbent body 44 (FIG. 3) disposed on the inner surface of the article relative to the outercover 40 for absorbing liquid body exudates. For example, the absorbent body 44 can be located between the outercover 40 and the bodyside liner 42. The bodyside liner 42 and the outercover 40 can be attached to each other by adhesive, ultrasonic bonding, thermal bonding or by other suitable attachment techniques known in the art. Moreover, at least a portion of the absorbent body 44 can optionally be attached to the bodyside liner 42 and/or the outercover 40 utilizing the methods described above. The liner 42 can be coextensive with the outercover 40 or can be larger or smaller than the outercover 40. For example, the liner 42 can be optionally be similar in size to the absorbent body 44, or may be configured to wrap the absorbent body 44 only.

The diaper 20 can optionally include a pair of containment flaps (not shown) for inhibiting the lateral flow of body exudates. The containment flaps can be operatively attached to the diaper 20 in any suitable manner as is well known in the art. In particular, suitable constructions and arrangements for the containment flaps are generally well known to those skilled in the art and are described in U.S. Pat. No. 4,704,116 issued Nov. 3, 1987 to Enloe, which is incorporated herein by reference to the extent that it is consistent (i.e., not in conflict) herewith.

To further enhance containment and/or absorption of body exudates, the diaper 20 may optionally include waist elastic members 54 in the front and/or back waist regions 22 and 24 of the diaper 20. Likewise, the diaper 20 may optionally include leg elastic members 58, as are known to those skilled in the art. The waist elastic members 54 and the leg elastic members 58 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

As can be readily appreciated, one or more elements such as the containment flaps, waist elastics and leg elastics can alternatively be omitted from the diaper 20 to reduce material costs and product complexity. As such, the process for producing the diaper 20 can be simplified and executed at a high speed.

The chassis side edges 90 of the diaper 20 of the present invention can optionally be partially inflected. In such an aspect, the inflected chassis side edges 90 can provide an effective, low cost barrier leg cuff that can advantageously seal about the leg of the wearer in use and help restrict the lateral flow of bodily exudates for improved performance. For example, as representatively illustrated in FIGS. 2-3, each of the chassis side edges 90 can be directed in the lateral direction 48 inboard toward the inner surface 28 of the diaper 20. The inboard directing of the chassis side edges can occur at any point along the length of the chassis side edges 90 in the longitudinal direction 46. As such, the chassis side edges 90 can be at least partially inflected, or in certain aspects, substantially the entire length of the chassis side edges 90 in the longitudinal direction 46 can be inflected.

In aspects where the diaper 20 features inflected chassis side edges 90 (FIGS. 2-3) the chassis waist edges 92 and 94 can define a width differential. For example, the chassis front waist edge 94 can define a chassis front waist edge width in the lateral direction 48, indicated at the arrow marked 95. Similarly, the chassis back waist edge 92 can define a chassis back waist edge width in the lateral direction 48, indicated at the arrow marked 93. Accordingly, the chassis back waist edge width 93 can be different than the chassis front waist edge width 95. In particular, the chassis back waist edge width 93 can be greater than the chassis front waist edge width 95. In a particular aspect, the chassis back waist edge width 93 can be at least 10%, greater than the chassis front waist edge width 95, and in certain aspects 25% to 30% greater than the chassis front waist edge width 95. Such tapering of the absorbent chassis 32 from the chassis back waist edge 92 to the chassis front waist edge 94 can advantageously improve the fit of the diaper 20 upon the wearer, particularly in the crotch region 26.

The outercover 40 may suitably include a material that is substantially liquid impermeable. The outercover 40 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outercover 40 may include a woven or non-woven fibrous web layer that has been totally or partially constructed or treated to impart the desired levels of liquid impermeability to selected regions that are adjacent or proximate the absorbent body.

The outercover 40 may also be stretchable, and in some aspects it may be elastomeric. For example, such an outercover material can include a 0.3 osy polypropylene spunbond that is necked 60 percent in the lateral direction 40 and creped 60 percent in the longitudinal direction 48, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outercover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent body 44. A suitable liquid permeable bodyside liner 42 is a nonwoven polyethylene/polypropylene bicomponent web having a basis weight of about 27 gsm; the web may be spunbonded or a bonded carded web. Optionally, the bodyside liner 42 may be treated with a surfactant to increase the wettability of the liner material.

Alternatively, the bodyside liner 42 may also be stretchable, and in some aspects it may be elastomeric. For instance, the liner 42 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., which is incorporated by reference herein to the extent that it is consistent (i.e., not in conflict) herewith.

The absorbent body 44 is suitably compressible, conformable and capable of absorbing and retaining liquid body exudates released by the wearer. For example, the absorbent chassis can include a matrix of absorbent fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The absorbent body 44 can be in a variety of shapes and configurations as are known in the art, such as rectangular, hourglass shaped, I-shaped, and the like. In addition, the absorbent body 44 can have a density within the range of about 0.10 to about 0.5 grams per cubic centimeter and may be wrapped or encompassed by a suitable tissue or nonwoven wrap for maintaining the integrity and/or the shape of the absorbent chassis.

In one aspect, the absorbent body 44 may be stretchable so as not to inhibit the stretchability of other components to which the absorbent body may be adhered, such as the outercover 40 and/or the bodyside liner 42. For example, the absorbent body may include materials disclosed in U.S. Pat. Nos. 5,964,743, 5,645,542, 6,231,557, 6,362,389, and international patent application WO 03/051254, the disclosure of each of which is incorporated by reference herein.

In some aspects, a surge management layer (not shown) may be included in the diaper 20. The surge management layer may be positioned in the diaper 20 in a variety of locations as is known in the art. For example, the surge management layer can be proximate the absorbent body 44, for example between the absorbent body 44 and the bodyside liner 42, and attached to one or more components of the diaper 20 by methods known in the art, such as by adhesive, ultrasonic bonding, pressure bonding, thermal bonding, and the like or combinations thereof.

A surge management layer helps to decelerate and diffuse surges or gushes of liquid that may be rapidly introduced into the absorbent body 44. Desirably, the surge management layer can rapidly accept and temporarily hold the liquid prior to releasing the liquid into the storage or retention portions of the absorbent body 44. Examples of suitable surge management layers are described in U.S. Pat. Nos. 5,486,166 and 5,490,846, the contents of which are incorporated herein by reference to the extent that they are consistent (i.e., not in conflict) herewith.

As mentioned above, the various aspects of the diaper 20 of the present invention can also include a pair of back ears 134 (FIGS. 1-3). The back ears 134 include a back ear proximal edge 80, an opposed back ear distal edge 82, a back ear first connecting edge 84 and a back ear second connecting edge 86.

In addition, the diaper 20 can optionally also include a pair of front ears 34 (FIGS. 2-3). The front ears 34 include a front ear proximal edge 70, an opposed front ear distal edge 72, a front ear first connecting edge 74 and a front ear second connecting edge 76.

The proximal edges 70, 80 are the portion of the ears 34, 134 that are attached proximate the chassis side edges 90 in the respective waist regions 22, 24. The distal edges 72, 82 are those edges of the ears 34 and 134 that are opposite the proximal edges 70, 80 moving in a direction outboard from the absorbent chassis 32. The first and second connecting edges 74, 76, 84, 86 connect the proximal edges 70, 80 and the distal edges 72, 82 of the ears 34 and 134.

The ears 34 and 134 may be attached to the absorbent chassis 32 in a variety of ways as are known in the art. For example, the ears 34, 134 may be attached to the absorbent chassis 32 with adhesive, ultrasonic bonds, pressure bonds, thermal bonds, and the like, or combinations thereof. In addition, the ears 34 and 134 may be attached to the absorbent chassis 32 on the inner surface 28 of the diaper 20 (FIG. 2-3), the outer surface 30 of the diaper 20, or can be sandwiched between at least some of the layers that can make up the absorbent chassis 32, such as the outercover 40 and liner 42. Moreover, the ears 34, 134 may be attached in various combinations. For example, the front ears 34 can be attached to the absorbent chassis 32 on the inner surface 28 of the diaper 20 while the back ears 134 can be attached to the absorbent chassis 32 on the outer surface 30 of the diaper 20.

Figure 4:
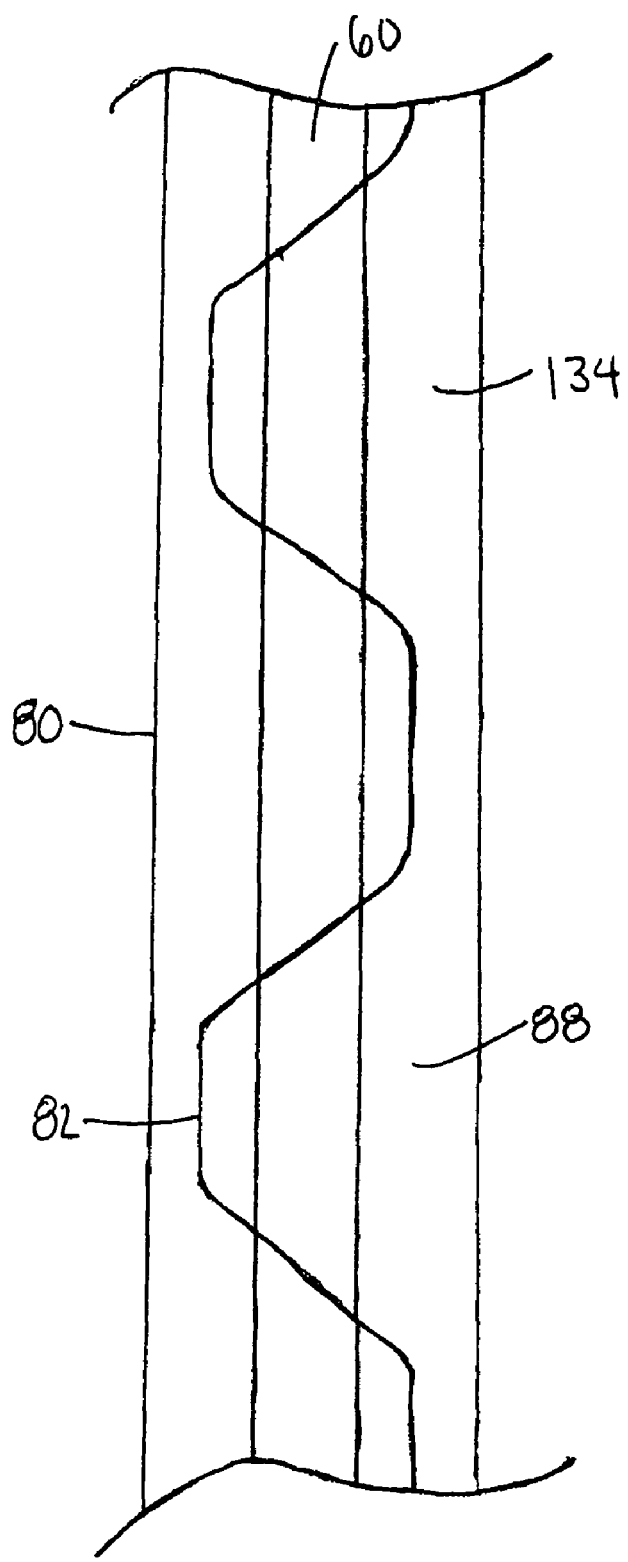
FIG. 4 representatively illustrates a plan view of an interconnected web of ears defining complementary shapes and suitable for use with the diaper of the present invention.

The ears 34 and 134 of the present invention can include and/or be formed from a base material (FIG. 2-4). For example, the front ears 34 can include a front ear base material 78 and the back ears can include a back ear base material 88. The base materials 78, 88 may be provided by materials as are known in the art such as woven materials, nonwoven materials, or combinations thereof. In a particular aspect, at least a portion of the base materials 78, 88 are an elastomeric material capable of elongating in at least the lateral direction 48 to provide elastomeric ears 34 and 134. Examples of a suitable elastomeric material for use in connection with the base materials 78, 88 are a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the base materials 78, 88 can optionally include nonstretchable materials or stretchable but inelastic materials. For example, the base material 78, 88 can include various nonstretchable nonwovens such as a spunponded material or a spunbond/meltblown/spunbond (SMS) material. Alternatively, the base materials 78, 88 can include film materials that could also be suitable for use in connection with the outercover 40. In yet another alternative, the base materials 78, 88 can include a combinations of various stretchable materials and/or nonstretchable materials.

The component layers making up the base materials 78 and 88 may be assembled in various ways as are known in the art. For example, the layers in the base materials 78, 88 can be assembled with adhesives, ultrasonic bonding, pressure bonding, thermal bonding, and the like or combinations thereof. Optionally, the base materials 78, 88 can be provided by a single layer of material. Suitable source webs for the ears 34, 134 are described in U.S. patent application Ser. No. 11/116,655, entitled COMPOSITE WEB filed in the name of Van Dyke, incorporated herein by reference to the extent that it is consistent (i.e., not in conflict) herewith.

As representatively illustrated in FIGS. 2-4, the ears 34 and 134 can also optionally include a fastening member 60 disposed thereon. For example, one of or each of the back ears 134 can include a fastening member 60 attached to the back ear base material 88. Optionally, one of or each of the front ears 34 can include fastening member 60 attached to the front ear base material 78. Moreover, the back ears 134 can include fastening member 60 while the front ears 34 do not, or vice versa. Still further, all of the ears 34 and 134 can include fastening member 60.

The fastening member 60 may include any refastenable fasteners suitable for absorbent articles, such as adhesive fasteners, cohesive fasteners, mechanical fasteners, or the like. In one aspect of the invention, the fastening member 60 is active fastening members for improved performance. Suitable active fastening members are interlocking geometric-shaped materials that are intended to engage another material such as hooks, bulbs, mushrooms, arrowheads, balls on stems, male mating components or the like. Accordingly, the fastening member 60 attached to the back ear base material 88 can be active fastening member. Likewise, the fastening member 60 attached to the front ear base material 78 can be active fastening member. One specific example of a fastening member is VELCRO HTH 858 or VELCRO HTH 823 available from Velcro Industries B.V., Amsterdam, Netherlands.

The fastening member 60 may be disposed on the ears 34, 134 to engage different portions of the diaper 20. For example, the fastening member 60 attached to the back ears 134 can be configured to engage the outer surface 30 of the diaper 20. In such a configuration, the fastening member 60 is attached to the back ear 134 on the inner surface 28 of the diaper 20. Further, the fastening member 60 attached to the front ear 34 can be configured to engage the inner surface 28 of the diaper 20. In such a configuration, the fastening member 60 is attached to the front ear 34 on the outer surface 30 of the diaper 20. Accordingly, the fastening member 60 on the ears 34, 134 may be configured to refastenably engage directly with the outercover 40 or the liner 42 of the diaper 20. Alternatively, at least one attachment panel (not shown) may be suitably located on the diaper 20 to which the fastening member 60 on the ears 34, 134 is configured to engage. For example, an attachment panel can be located on the outercover 40.

Thus, the fastening member 60 can be employed to attach the back waist region 24 of the diaper 20 to the front waist region 22 of the diaper 20 about the waist of the wearer. Accordingly, the waist edges 38 and 39 of the diaper 20 are configured to encircle the waist of the wearer to define the waist opening 50 of the diaper, while the side edges 36 of the diaper 20 define the leg openings 52 (FIG. 1).

Each of the fastening members can define a fastener proximal edge 62, an opposed fastener distal edge 64, a fastener first connecting edge 66 and a fastener second connecting edge 68. The fastener proximal edge 62 are the portion of the fastening member 60 that is proximate to the chassis side edges 90. The fastener distal edges 64 are those edges of the fastening member 60 that is opposite the proximal edge 62 moving in a direction outboard from the absorbent chassis 32. The fastener first and second connecting edges 66, 68 connect the proximal edge and the distal edge of the fastening member 60.

The ears 34 and 134 can further have a variety of shapes as are known in the art. For example, as representatively illustrated in FIGS. 2-4, the back ears 134 can have a complementary shape with each other. Similarly, front ears 34 can also have a complementary shape with each other. Moreover, as the front ears 34 can have complementary shapes with each other, and the back ears 134 can simultaneously have complementary shapes with each other, but the front ears 34 can optionally have a different shape than the back ears 134 (FIG. 2-4). This may be desirable as the front ears 34 may have a different purpose than the back ears 134, or it may be desirable from an aesthetic or material cost perspective. Alternatively, the front ears 34 and back ears 134 may optionally have a substantially similar shape.

In the various aspects of the present invention, the first connecting edges 74 and 84 of the ears 34 and 134 can advantageously be substantially flush with the chassis waist edges 92 and 94. As used herein the phrase "substantially flush" refers to the first connecting edges 74 and 84 of the ears 34 and 134 being even, at least at the point of attachment, with the respective waist edges 92 and 94 in the waist region 22, 24 where the ear 34 and 134 is attached. The first connecting edge 74 or 84 of the ears 34 and 134 of the present invention will be considered "substantially flush" with the chassis waist edges 92 and 94 while taking into account shifting or retraction of the materials that comprise the absorbent chassis 32 that may occur during processing. For example, an amount attributable to such shifting or retracting of materials during processing is 2 mm, and as such, the first connecting edge 74 or 84 of the ears 34 and 134 will be considered "substantially flush" with the chassis waist edges 92 and 94 if they are within 2 mm of the respective chassis waist edge 92 and 94.

For example, as representatively illustrated in FIGS. 2-3 the back ear first connecting edges 84 can be substantially flush with the chassis back waist edge 92. In a particular aspect, the back ear first connecting edges 84 of each of the back ears 134 can be completely flush with the chassis back waist edge 92. Moreover, as representatively illustrated in FIGS. 2-3, each of the fastener first connecting edges 66 of each fastening member 60 disposed on the back ears 134 can be substantially flush with the respective back ear first connecting edge 84 of the back ear 134 on which each of the fastening members 60 are disposed.

Likewise, in aspects where the diaper 20 includes a front ear 34, the front ear first connecting edges 74 of each of the front ears 34 can be substantially flush with the chassis front waist edge 94 (FIGS. 2-3). In a particular aspect, the front ear first connecting edges 74 of each of the front ears 34 can be completely flush with the chassis front waist edge 94. Moreover, as representatively illustrated in FIGS. 2-3, each of the fastener first connecting edges 66 of each fastening member 60 disposed on the front ears 34 can be substantially flush with the respective front ear first connecting edge 74 of the front ear 34 on which each of the fastening members 60 are disposed.

Alternatively, the fastening members 60 can optionally be located completely within the respective edges 70, 72, 74, 76, 80, 82, 84, 86, of the front ear 34 and/or back ear 134. In such a configuration, the fastening members 60 can be cut and placed within the perimeter of the ear 34, 134, prior to the ears 34, 134 being attached to the absorbent chassis 32 or after the ears 34, 134 are attached to the absorbent chassis 32.

The ears 34, 134 can be placed on the absorbent chassis 32 in connected pairs when the absorbent chassis 32 are joined in a web configuration at an intermediate point of the production process (FIG. 3). The ears 34 and 134 can then be separated into individual ears 34 and 134 when the web of joined absorbent chassis 32 is separated into individual absorbent chassis 32. Accordingly, this can simplify the process for applying the ears 34 and 134 to the absorbent chassis 32 as compared to applying each ear 34, 134 to the chassis 32 individually. As such, the process for producing the diapers 20 can be simplified, and likewise, the speed with which the diapers 20 are produced can be potentially increased.

Further, the chassis back waist edge 92 and the back ear first connecting edges 84 of each of the back ears 134 can optionally define a linear article back waist edge 38. Similarly, the chassis front waist edge 94 and the front ear first connecting edges 74 of each of the front ears 34 can optionally define a linear article front waist edge 39. As used herein the terms "linear article back waist edge" and "linear article front waist edge" refers to a relationship between the first connecting edges 74 and 84 of the respective ears 34 and 134 and the respective chassis waist edges 92 and 94 where all the edges extend substantially in the same line, as representatively illustrated in FIGS. 2-3.

The various aspects described above lend themselves to producing a diaper 20 in a front-front, back-back arrangement. That is, the chassis front waist edge 94 of one diaper 20 is adjoining the chassis front waist edge 94 of an adjacent diaper 20 during manufacture (FIG. 3). Similarly, the article front waist edge 39 of one diaper 20 can be adjoining the article front waist edge 39 of an adjacent diaper 20 during manufacture. Likewise the chassis back waist edge 92 of one diaper 20 is adjoining the chassis back waist edge 92 of an adjacent diaper 20 during manufacture (FIG. 3). Similarly, the article back waist edge 38 of one diaper 20 can be adjoining the article back waist edge 38 of an adjacent diaper 20 during manufacture. In particular, the combination of the substantially rectangular absorbent chassis 32 along with arranging the ears 34 and 134 in one or more of the aspects as described above can suitably result in an efficient, straightforward process while utilizing the front-front, back-back arrangement of diapers 20. In particular, the front-front, back-back arrangement can offer a number of processing advantages such as simplifying the registration of the ears 34 and 134 with the chassis waist edges 92 and 94. In addition the arrangement allows an easier discontinuity of width between the front waist region 22 and the back waist region 24 of the diaper 20, providing additional product configuration options.

Further, configuring the ears 34 and 134 to have complementary shapes can reduce material costs by eliminating trim waste. Moreover, since the complementary shapes can allow the ears 34, 134 to be cut from a single web (FIG. 4), a combination of one or more of the aspects described above can advantageously contributed to increased diaper production efficiency and speed while potentially reducing product and production costs.

Turning now to FIG. 5, the present invention is also directed to a package 97 that contains a plurality of the diapers 20 as described above and illustrated in FIGS. 1-3. The package 97 can contain at least three diapers 20, and suitably can contain from 10 to 96 or more diapers 20. Packaging suitable for use with the diaper 20 is well known in the art and for example is described in U.S. Pat. No. 6,318,555 issued Nov. 20, 2001, to Kuske et al., the disclosure of which is hereby incorporated by reference to the extent that it is consistent (i.e., not in conflict) herewith. The package 97 can be suitably provided by a polymer film material that is sufficiently flexible to assume a generally hexahedral shape when the package 97 is filled with diapers 20. Alternatively, other suitable materials or shapes may be utilized for the package 97 as are known in the art.

As discussed above, the diapers 20 can be configured to be particularly suited for a front-front, back-back production process. Accordingly, as representatively illustrated in FIG. 5, the diapers 20 can be advantageously arranged within the package 20 such that the front waist region 22 of a first diaper can be in a facing relationship with the front waist region 22 of a first adjacent diaper. Similarly, the back waist region 24 of the first diaper can be in a facing relationship with the back waist region 24 of a second adjacent diaper (FIG. 5). As such, at least a portion of the diapers 20 can be arranged within the package to define a front-front, back-back article packaging pattern. Suitably, in packages containing more than three diapers 20, this front-front, back-back article packaging pattern can be repeated a plurality of times within the package, and still more suitably, the front-front, back-back article packaging pattern exists through the entire array of diapers 20 within the package 97.

The front-front, back-back article packaging pattern can be advantageously used within the package 97 of diapers 20 to reduce the number of steps and amount of equipment associated with the diaper production and packaging process. That is, as mentioned above, the diaper 20 of the present invention can be configured to be particularly suited to a front-front, back-back arrangement during production (FIG. 3). Accordingly, in aspects where the diapers 20 are produced in such a manner, it can be advantageous to package the diapers 20 in such an arrangement so that additional process steps can be avoided to place the diapers 20 in the more traditional back-front packaging pattern. As such the efficiency of the process is improved and reducing production costs can be reduced and production speeds can be increased.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article defining a lateral direction and a longitudinal direction perpendicular to said lateral direction, a back waist region, a front waist region and a crotch region connecting the back waist region and said front waist region, a linear article back waist edge and a linear article front waist edge, an inner surface and an outer surface opposite said inner surface, said absorbent article comprising:

An absorbent chassis defining a chassis back waist edge and a chassis front waist edge opposite said chassis back waist edge, a pair of chassis side edges extending in said longitudinal direction, and a substantially rectangular chassis shape wherein said chassis front waist edge defines a chassis front waist edge width and said chassis back waist edge defines a chassis back waist edge width and wherein said chassis back waist edge width is greater than said chassis front waist edge width, said absorbent chassis comprising:

A liquid impermeable outercover, and

An absorbent body disposed on said outercover;

A back ear formed separately from and attached proximate each of said chassis side edges in said back waist region, each of said back ears comprising a back ear proximal edge, a back ear distal edge, a back ear first connecting edge and a back ear second connecting edge, wherein said back ear first connecting edge and said back ear second connecting edge connect said back ear proximal edge and said back ear distal edge and wherein said back ear first connecting edges of each of said back ears are substantially flush with said chassis back waist edge; and A fastening member disposed on said inner surface of each of said pair of back ears.

2. The absorbent article of claim 1 wherein each of said fastening members defines a fastener first connecting edge, a fastener second connecting edge, a fastener proximal edge and a fastener distal edge wherein said fastener first connecting edge and said fastener second connecting edge connect said fastener proximal edge and said fastener distal edge and wherein each of said fastener first connecting edges are substantially flush with said back ear first connecting edge on which each of said fastening members are disposed.

3. The absorbent article of claim 1 further comprising a front ear formed separately from and attached proximate each of said chassis side edges in said front waist region, each of said front ears comprising a front ear proximal edge, a front ear distal edge, a front ear first connecting edge and a front ear second connecting edge, wherein said front ear first connecting edge and said front ear second connecting edge connect said front ear proximal edge and said front ear distal edge and wherein said front ear second connecting edges of each of said front ears are substantially flush with said front waist edge.

4. The absorbent article of claim 3 further comprising a fastener member disposed on each of said front ears.

5. The absorbent article of claim 3 wherein said chassis front waist edge and said front ear first connecting edges of each of said front ears define said linear article front waist edge.

6. The absorbent article of claim 3 wherein said front ears have a complementary shape with each other.

7. The absorbent article of claim 1 wherein each of said chassis side edges are at least partially inflected.

8. The absorbent article of claim 1 wherein said back ears have a complementary shape with each other.

9. The absorbent article of claim 1 wherein said chassis back waist edge and said back ear first connecting edges define said linear article back waist edge.

10. The absorbent article of claim 1 wherein said chassis side edges are rectilinear edges.

* * * * *